(12) United States Patent
Aseere

(10) Patent No.: US 7,810,397 B2
(45) Date of Patent: Oct. 12, 2010

(54) TUFT GRIPPING STRENGTH TEST METHOD AND APPARATUS FOR CARPET PRIMARY BACKING MATS

(75) Inventor: Lester Mickel Aseere, Parker, CO (US)

(73) Assignee: Johns Manville, Denver, CO (US)

( * ) Notice: Subject to any disclaimer, the term of this patent is extended or adjusted under 35 U.S.C. 154(b) by 281 days.

(21) Appl. No.: 12/231,146

(22) Filed: Aug. 29, 2008

(65) Prior Publication Data
US 2010/0050780 A1    Mar. 4, 2010

(51) Int. Cl.
*G01N 3/08*    (2006.01)
(52) U.S. Cl. .......................................... 73/827; 73/760
(58) Field of Classification Search ............ 73/760–827
See application file for complete search history.

(56) References Cited

U.S. PATENT DOCUMENTS 3,965,737 A * 6/1976 Matthews ..................... 73/160
5,710,426 A * 1/1998 Reed et al. .............. 250/237 G
5,795,990 A * 8/1998 Gitis et al. ........................ 73/9
7,475,601 B2 * 1/2009 Dreiling et al. ............... 73/827

* cited by examiner

*Primary Examiner*—Max Noori
(74) *Attorney, Agent, or Firm*—Robert D. Touslee

(57) ABSTRACT

A test method for measuring yarn and tuft or loop gripping strength characteristics and capability of tufted nonwoven primary backing mats for making tufted carpets, the tufted primary backing mat having no additional binder or adhesive on the backside of the mat prior to making tufted carpet is disclosed. The test apparatus and test method can be used for quality control purposes and for evaluation of experimental or new candidates for primary backing mats for making interim tufted products for carpets that are more resistant to tuft or loop defects. Revealed is a new and critical Quality Knee characteristic of primary backing mats that is crucial for minimizing tuft or loop defects during the tufting process and also the force magnitude on the yarn necessary to pop the tuft completely out of the primary backing mat sample.

15 Claims, 8 Drawing Sheets

TUFT GRIPPING STRENGTH TEST METHOD AND APPARATUS FOR CARPET PRIMARY BACKING MATS

The invention involves a superior test apparatus and method for determining the capability of carpet primary backing mats to grip strands of yarn forming tufts or loops in an interim tufted product before any additional adhesive or binder is applied to the backside of the tufted interim product.

BACKGROUND

In the manufacture of tufted carpet a fibrous nonwoven or woven primary mat, e.g. a spunbonded mat, of more than 2-4 meters in width, is run through a tufting machine and tufted. Normally, this produces a tufted interim product that may be rolled up and put into storage until an order for that type and color of tufted carpet is received for the carpet finishing line. The tufts are held in the carpet primary backing mat only by the friction of the primary backing mat on the strands of yarn penetrating the mat. When the tufting needles penetrate the primary backing mat each needle carries with it two carpet yarn strands forming a tuft or loop beneath the lower surface of the primary backing mat. As soon as tufts or loops are formed, a hook mounted beneath the primary backing mat enter each tuft or loop and hold each tuftor loop to the desired height while the tufting needles are withdrawn to a location above the primary backing mat, then the hooks are withdrawn from the tufts or loops and the primary backing mat is moved to expose the untufted primary backing mat for the next row of tufts or loops to be formed by repeating the above process.

In the tufting process, the tufting machine will either leave the tufts or loops as-is or, on loop pile machines, will pull the strand of the yarn from selected ones of the last tuft or loop some to reduce the size/heights of selected ones of the just formed tufts or loops (the latter being most typical to make textured carpet). During this controlled shortening of selected tufts or loops a desired amount is accomplished by limiting the length of new yarn for the next row of tufts in known manner, thus causing the remainder of the next tuft or loop to be pulled from the previous tuft or loop thereby making the tuft or loop shorter than its original height. Since each tufting needle makes a hole in the primary backing mat large enough for the two strands of yarn and the tufting needle, the hole, after the tufting needle is withdrawn, is larger than desired to properly grip and hold the strands of yarn. If each hole does not close up sufficiently to a smaller size to grip the yarn sufficiently, the momentum of the pulling of the strand of yarn to shorten tufts or loops length will overpull causing loops or tufts to be too short or to completely pop out of the hole. Any of these undesirable tuft or loop defects, if not corrected by costly labor and time, will produce a defect in the finished carpet. Further, a primary backing mat that does grip the yarn strands sufficiently during the tufting process will produce a more accurate carpet face texture.

The tufted interim product is then wound up, transported to storage or a tip shearing line where it is unwound, tip sheared, wound back up, transported again to storage or a carpet finishing line where it is unwound, adhesive is applied and rewound. During these handling steps the tufts are exposed to snags and other forces that can cause poorly gripped yarn strands to pull partially or all of the way out of holes in the primary backing mat, either individually or in groups of two or more in a tuft row since the yarn strands are held in each hole only by the tuft gripping capability of the primary backing mat. A costly problem the carpet industry has in handling the rolls of tufted interim products is that sometimes one or more tufts is contacted by something on the production line or in transit to and from storage that pulls out one or more tufts and ruins the roll, or at least a section of the roll of interim product. This also happens sometimes in the tufting process. This happens with some primary backing mats more than others. Thus there is a need to determine accurately the capability of the primary backing mat to grip the tufts so that this property of the mat can be increased and so that during manufacture of the primary backing mat this property can be checked periodically for process and quality control purposes. Especially for the latter purpose it is important that the test can be performed quickly and with the least labor required.

Tests do exist for measuring the Tuft Withdrawal Force or Grab Strength for finished tufted carpet products, such as ASTM D-1335 or AWTA Test Code T-34, but in the finished carpet the magnitude of force required to remove a tuft is magnitudes higher and is done for a totally different reason, i.e. to determine how well the carpet will resist vacuum cleaners and wear and tear that tends to pull on the tufts. This test is not sufficient for an interim tufted product, and the use of such a test to improve the characteristics of the primary backing for holding tufts in place is sorely needed.

A test for measuring the tuft gripping strength of primary backing mats having no adhesive or binder added after tufting is disclosed in Published Patent Application No. 20070137294. This test requires more steps, including using a tufting machine to tuft a much larger sample of primary backing mat than is necessary for the test, taking more time and material per sample. It has recently also been discovered that the results of that test are less than fully indicative of the tuft gripping strength of the primary backing mats in typical industrial carpet making processes because it requires pulling the tufted loop in a direction opposite to the direction of the yarn pulls on a loop pile tufting machine, the action causing short tuft defects in tufted interim products.

SUMMARY

In the tufting process to make an interim tufted product, the primary backing mat is indexed after every tufting cycle and since the yarn is suspended between the tufting needles and the last loops formed, and to form a textured carpet having differing tuft heights, a yarn tension is created during the index that pulls selected strands connected to just formed tufts or loops to shorten those tufts or loops after the loop retainer hooks are withdrawn. Further, accidental or unintentional snags that shorten or pull out the tufts or loops completely can occur due to a hold down shoe that keeps the tufted interim product snug on the tufting table below the primary backing mat and other things that might snag the yarn from the side opposite the loops side of the tufted interim product on the tufting line, on the windup or during transporting from the tufting line to storage, from storage to the carpet finishing line or on the carpet finishing line before the adhesive is applied to the backside of the interim tufted product to lock in the loops to the primary backing mat. Such snags that pull the yarn and shorten the loops cause costly defects that must either be repaired with costly labor and delays or must be cut out of the carpet and the carpet spliced. The yarn or tuft gripping strength property or properties of the primary backing mat is very important to eliminate or substantially reduce the frequency of all of these types of defects.

It has been discovered that the yarn or tuft gripping capabilities of the primary backing mat, to be truly indicative of the capability of the primary backing mat to resist undesirable excessive yarn pulls and/or snags, etc. must be measured by pulling one loose end portion of the yarn forming a tuft or loop from the surface of the primary backing mat that the tufting needle and yarn first enters the primary backing mat to form the tuft or loop, and most typically to do so by pulling a loose end portion of the yarn generally parallel to the top surface of the primary backing mat sample. By generally parallel is meant very near the needle entering surface of the primary backing mat, most typically as close to that surface as practical without the surface of the yarn being pulled from contacting the entering surface of the primary backing mat significantly to cause friction drag that would give a false gripping capability test result. Thus a yarn gripping clamp holding and pulling the one loose strand of yarn will be a distance somewhat higher than at least one-half the diameter of the yarn strand and high enough that no part of the yarn strand between the yarn clamp and the needle entering surface of the mat at the tuft hole contacts the entering surface of the primary backing mat and also high enough above the entering surface that no part of the force measuring device holding the yarn clamp contacts the entering surface of the primary backing mat.

In the test method disclosed in Published Patent Application No. 20070137294, the loop formed by the tufting needle is pulled from the primary backing mat from the primary backing mat from the surface that is last penetrated by the tufting needle and is pulled in a generally perpendicular direction to that surface of the primary backing mat, i.e. in a different direction than how the loop pile machine pulls the yarn from the tufts or loops. It has now been discovered that the capability of the critical tuft gripping strength of the primary backing mat can best be determined by pulling the yarn in a generally parallel direction to the surface of the primary backing mat that the tufting needle and yarn first enter the primary backing mat to form each tuft or loop. By doing so, it has also been discovered that there are two separate tuft gripping capabilities that are critical to eliminating or substantially reducing the tuft or loop defects in the interim tufted product. The first tuft gripping capability of the primary backing mat, called a Quality Knee, is its capability to hold the yarn snugly during indexing of the primary backing mat after the formation of each row of tufts to prevent overshortening of the tufts or loops during indexing due to the momentum of the yarn pulling action. The second tuft gripping capability of the primary backing mat, called here the Defect Peak, is its capability to grip the yarn of the tufts or loops sufficiently to prevent snags from pulling one or more tufts or loops completely out of the primary backing mat, a defect that is impossible or much more difficult to repair. The apparatus and method of determining a truly indicative TGS of the primary backing mat described below are based on these discoveries.

The invention includes an apparatus for quickly and accurately measuring the capability of a primary backing mat to grip a tuft or loop of yarn in a manner that resists snags that pull the yarn and shorten or remove the loops causing defects in the tufted interim product, and if not repaired, defects in the final tufted carpet or carpet tiles. The apparatus comprises;

a) a table or flat surface having an opening therein to support a primary backing mat test sample and that allows a tufting needle to pass therethrough, b) a first clamp on a first side portion of the table or flat surface to secure a test sample of primary backing mat, c) a second clamp that is movable on an opposite side of the table or flat surface for securing the test sample spaced from the first clamp, the second clamp being movable to apply a desired tension on the test sample, d) a mechanism for moving the second clamp to apply a desired tension force on the test sample, e) a movable tufting needle holder for holding a tufting needle and for moving the tufting needle in a generally perpendicular position with respect to the first surface of the test sample to cause the tufting needle and a length of yarn passing therethrough to penetrate the first surface of the test sample, the test sample and the second surface of the test sample and to form a loop of yarn extending from the second surface of the test sample, f) a tufting needle, g) a movable tuft or loop keeper for holding and moving a loop keeper into and out of a loop keeping position, h) a tuft or loop keeper for holding the loop extending from the second surface of the test sample while the tufting needle is withdrawn generally perpendicular to the first surface of the test sample out of the test sample, i) a yarn clamp located adjacent and above the first surface of the test sample for securing an end part of the length of yarn and located sufficiently above the first surface that the yarn portion between the yarn clamp and the location where the yarn emerges through the first surface of the test sample does not contact the first surface of the test sample over a significant portion of the yarn portion, j) a force measuring device for holding the yarn clamp and for measuring continuously the force required to pull the length of yarn, including the loop, out of the test sample, k) a mechanism for moving the force measuring device holding the yarn clamp in a direction generally parallel to the first surface of the mat until the loop is pulled out of the test sample and l) a device for recording the continuous force measured by the force measuring device.

By generally perpendicular is meant plus or minus about 5 degrees from true perpendicular. By generally parallel is meant within about 5 degrees from true parallel. By a generally consistent speed is meant that the speed varies no more than about +/−0.25 inch/second.

The test method comprises;

a) applying a desired tension onto a strip of primary backing mat, a test sample, b) forcing a tufting needle holding a length of yarn through a first surface, thickness and a second surface of the test sample in a generally perpendicular direction to the first and second surfaces of the test sample to form a loop of yarn extending from the second surface of the test sample, c) holding the loop of yarn in place while the tufting needle holding the length of yarn is withdrawn, in a generally perpendicular direction to the second and first surfaces of the test sample, from the test sample, d) placing one end portion of the length of yarn extending from the first surface of the test sample into a third clamp mounted above and near the first surface, the third clamp being attached to a force measuring device, e) moving the third clamp in a direction generally parallel to the first surface and away from the tuft in the test sample at a generally consistent speed while continuously measuring and recording the force necessary to pull the length of yarn from the test sample and to completely remove the loop from the second surface and the first surface of the test sample.

By generally perpendicular is meant plus or minus about 5 degrees from true perpendicular. By generally parallel is meant within about 5 degrees from true parallel. By generally consistent speed is meant a variation of no more than about +/−0.25 inch per second.

When the word "about" is used herein it is meant that the amount or condition it modifies can vary some beyond that stated so long as the advantages of the invention are realized. Practically, there is rarely the time or resources available to very precisely determine the limits of all the parameters of one's invention because to do so would require an effort far greater than can be justified at the time the invention is being developed to a commercial reality. The skilled artisan understands this and expects that the disclosed results of the invention might extend, at least somewhat, beyond one or more of the limits disclosed. Later, having the benefit of the inventors' disclosure and understanding the inventive concept and embodiments disclosed including the best mode known to the inventor, the inventor and others can, without inventive effort, explore beyond the limits disclosed to determine if the invention is realized beyond those limits and, when embodiments are found to be without any unexpected characteristics, those embodiments are within the meaning of the term "about" as used herein. It is not difficult for the artisan or others to determine whether such an embodiment is either as expected or, because of either a break in the continuity of results or one or more features that are significantly better than reported by the inventor, is surprising and thus an unobvious teaching leading to a further advance in the art.

DETAILED DESCRIPTION OF THE BEST MODE AND SOME OTHER EMBODIMENTS

Figure 1:
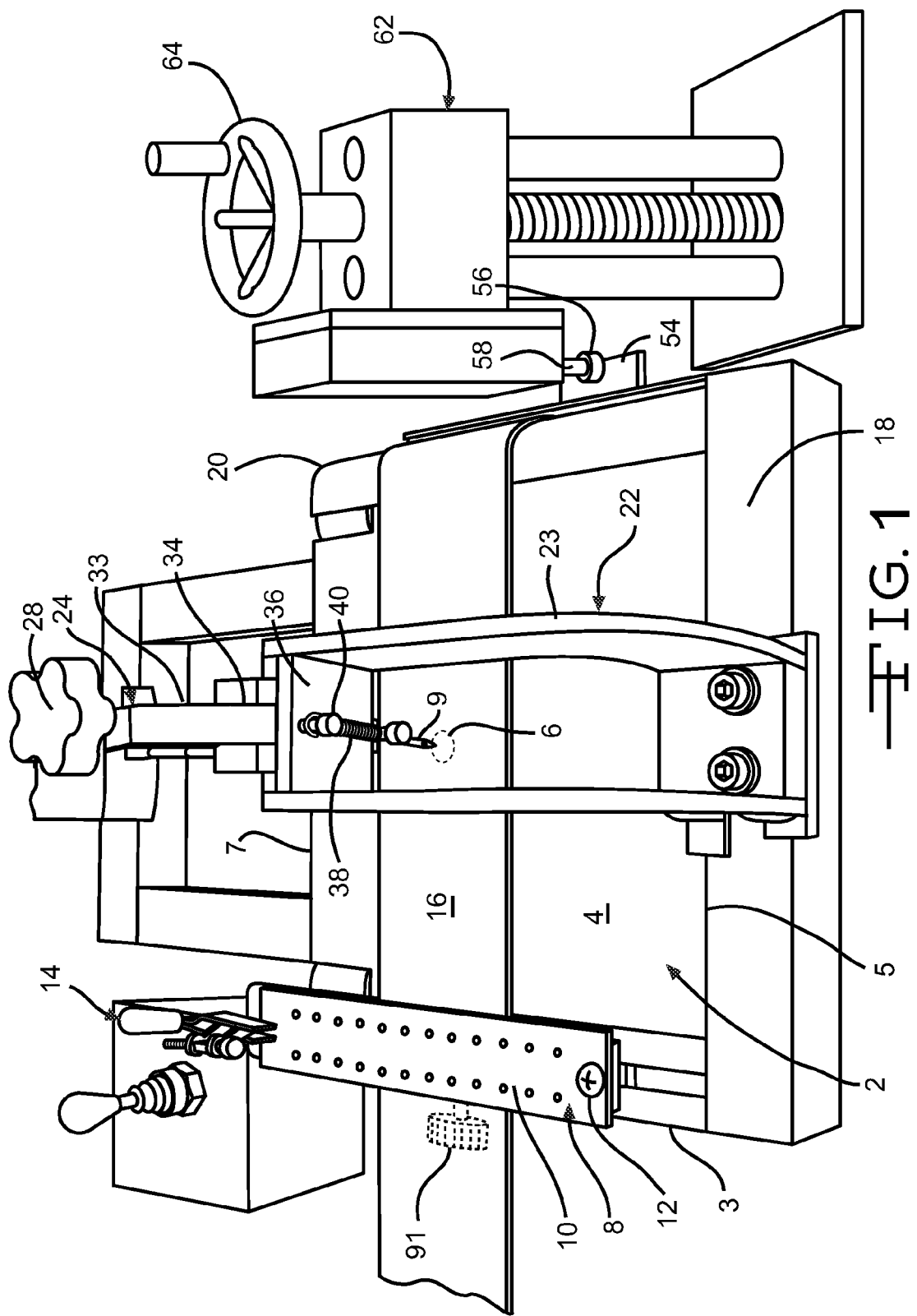
FIG. 1 is a partial perspective view of the apparatus of the invention.

FIG. 1 shows most of the apparatus of the invention in perspective. A top 2, typically a flat surface 4, most typically a top of a table, but it is not necessary that the top surface be completely flat so long as it supports the sample during a tufting operation that will be described later. The top 2 or flat surface 4 has a hole 6 to permit a tufting needle 9 to pass through the top 2 or flat surface 4. The hole 6 is most typically round but can be any reasonable shape, and any reasonable size, so long as it permits tufting while supporting a primary backing mat sample 16 adequately during tufting. If the hole 6 is too large in a major dimension, it might allow the sample 16 to sag excessively during tufting. The top 2, or flat surface 4 comprises a first edge 3, a front edge 5, a rear edge 7 and a trailing edge 20. The trailing edge 20 can be an edge formed by two surfaces intersecting at 90 degrees, but more typically is a curved edge having a radius that permits a primary backing mat sample 16 to slide over the curved or radiused edge 20 under tension without damaging the sample.

A first clamp 8 lies along and on or near the first edge 3 for the purpose of securing the primary backing mat sample 16 from moving while a tension representative of the tension on primary backing mats in the tufting machines is applied. While this may vary somewhat depending on the machine itself and the different manners of operating the machines by various manufacturers, a representative tension has been found to be about 12 pounds applied to the sample. While the width of the test sample can vary, a 4 inch wide test sample produces consistent results and is the width used in the embodiments disclosed herein. The first clamp 8 shown comprises a top plate 10, an adjustable bolt 12 near one end of the top plate 10, a bottom plate 11 (see FIG. 3) and an adjustable, locking clamp 14 positioned to bias the ends of the top plate 10 and the bottom plate 11, opposite the ends held by the adjustable bolt 12, towards one another. A DeStaCo™ clamp is particularly usable for the adjustable, locking clamp 14. Also, it may be desirable to adhere a gripping surface to the sample contacting surfaces of the top plate 10 and the bottom plate 11 to provide better gripping of the primary backing mat sample. A thin piece of dense foam or a gripping particle containing paint are two of many possible things that can be used for this purpose.

An arm assembly 22 comprising an arm 23 is suspended above the top 2 and flat surface 4 and supports a plunger assembly 24. The plunger assembly 24 comprises a plunger member 26 having one end a knob 28 and on the other end a tufting needle holder 30 having a threaded gripping set screw 32 (see FIG. 5) to grip and secure the conventional tufting needle 9. The plunger member 26, such as a rod or any reasonable elongate member, is supported by a bracket 33 and the plunger member 26 is further guided by a hole in a second bracket 34 attached to a cross-member 36 attached to the arm 23, the plunger assembly 24 being positioned such that the tufting needle 9, in an upper position, is located above the hole 6 in the top 2. To keep the tufting needle 9 and the plunger member 26 in an upper position, a spring 38 is attached to a bolt or peg 40 fixed to the cross-member 36 and the other end of the spring attached to the set screw 32 on the tufting needle holder 30. When one presses the knob 28 down, the plunger member 26 moves down pushing the tufting needle 9 through the hole 6 (see FIG. 5), and when the downward force on the knob 28 is released, the spring 38 pulls the plunger member 26 and tufting needle 9 upward to a tufting needle position shown in FIG. 6.

Figure 2:
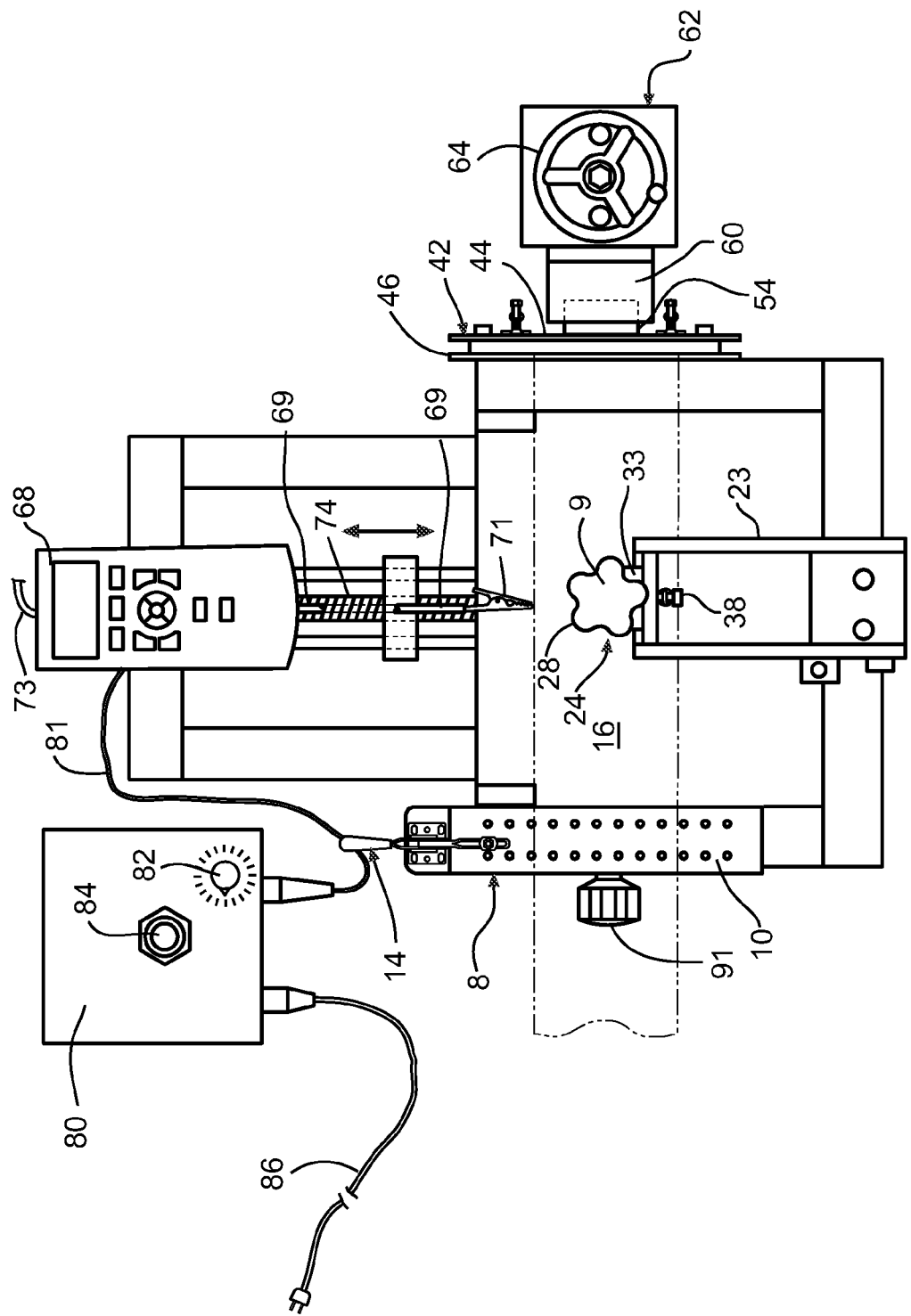
FIG. 2 is a plan view of the apparatus of the invention.
Figure 4:
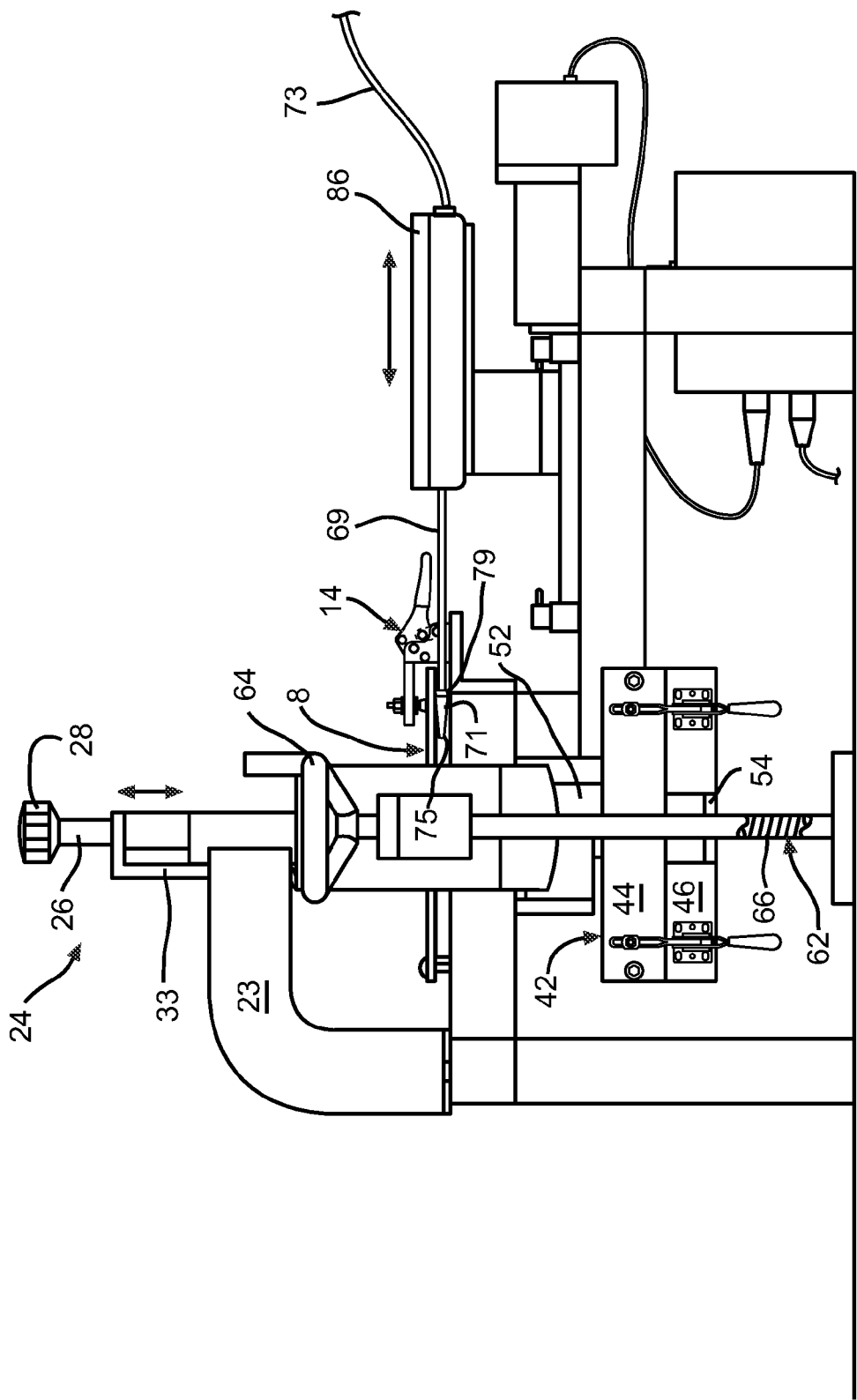
FIG. 4 is an opposite side view of the apparatus shown in FIGS. 1-3.

The apparatus also includes a, vertically mounted, second sample clamp 42 (see FIG. 4) comprising a vertically held top plate 44 and a vertically mounted bottom plate 46 with one or two clamps, one at or near each end of the top plate 44 and bottom plate 46, most typically DeStaCo clamps 48, 50. This second sample clamp 42 must be able to hold the primary backing mat sample 16 under a tension of at least about 12-15 lbs. Referring to FIGS. 1, 2 and 4, the second clamp 42 is vertically movable along a vertical support member 52 attached at its upper end to the top 2 or to a frame member supporting the flat surface 4. The sliding movement is conventional achieved in any one of many well known manners such as by bolt heads moving in a slot, on tracks or on vertical rods. Referring to FIGS. 1 and 4, a horizontal foot 54, mounted to a bottom edge of the bottom plate 46 on the second sample clamp 42 is contacted by a foot 56 attached to a measuring rod 58 of a force measuring gauge 60. Any force measuring gauge capable of measuring forces of at least about 0.5-15 lbs. is suitable, but and the force gauge most typically used is a Dillon Model GL 100 available from Precision Weighing Balances of Bradford, Mass. The force measuring gauge 60 is mounted on any force applying device that can apply a force of at least about 12 lbs. In the embodiment shown here, the force applying device is a conventional manual screw jack 62 having a rotating handle 64 that turns a screw 66 that when turned will move the horizontal foot 54, and the second sample clamp 42 to which it is attached, down to apply a tension to the primary backing mat sample 16.

Figure 3:
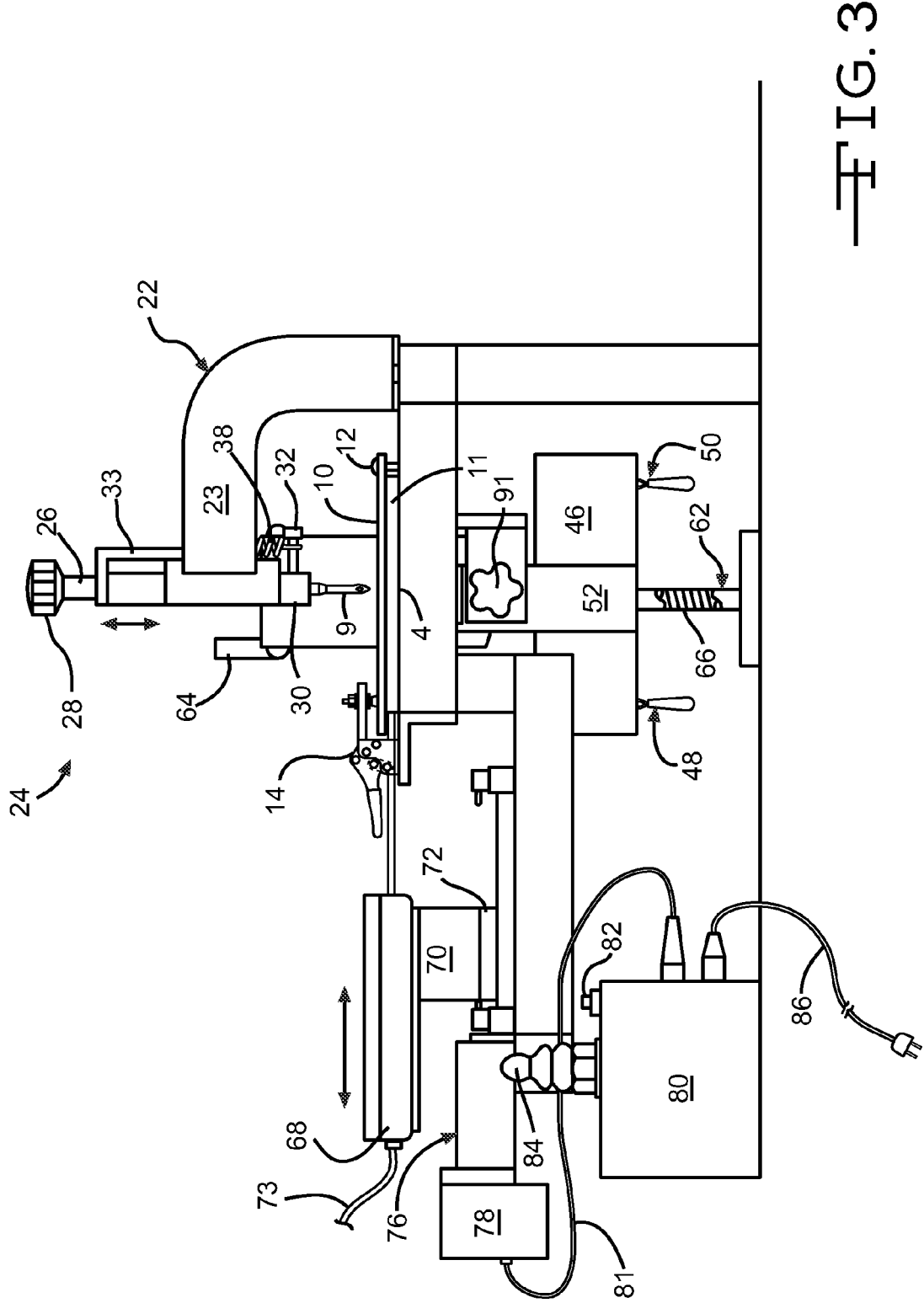
FIG. 3 is first side view of the apparatus shown in FIGS. 1 and 2.

Referring to FIGS. 2 and 3, a second force measuring gauge 68 is mounted on a vertical member 70 that is attached to a movable member 72 attached to a screw 74 driven by a screw drive 76 comprising an electric reversible and variable speed motor 78 controlled by a controller 80. A variable speed dial 82 on the controller can be rotated to set the desired speed of the screw drive 76 and a toggle control 84 is used to cause the screw drive 76 to move the second force gauge 68, its measuring rod 69 and a yarn clamp 71 away from the tufting needle 9 or towards the tufting needle 9. The yarn clamp 71 can be any type of clamp that is suitable for gripping one end of a piece of yarn extending from a tuft in the primary backing mat sample and in the embodiment shown in the drawings, an alligator clamp is attached to the end or end portion of the measuring rod 69 on the second force measuring gauge 68 as the yarn clamp 71. The second force gauge 68, measuring rod 69 and the yarn clamp 71 should be mounted such that the gripping portion 75 of the yarn clamp 71 is located just above the needle entering surface of the primary backing mat sample 16 and aligned with the tufting needle such that when an end portion of the yarn 88 is secured in the yarn clamp 71 and the yarn clamp 71 is moved away from the tufting needle 9 by the screw drive 76, the yarn 88 is pulled reasonably parallel to the surface of the primary backing mat sample 16. The second force measuring gauge 68 and its measuring rod 69 must also be mounted such that the lowest part 79 of the force measuring rod 69, or yarn clamp 71, does not contact the entering surface of the mat sample 16 when the yarn clamp 71 is moved towards or away from the tufting needle 9. The second force measuring gauge 68 can be any gauge capable of measuring a pulling force in the range of about zero to about 5-10 Newtons, and in the embodiment disclosed here a Chatillon Model DFS-002 available from Ametek®, Inc. of Largo, Fla., is used.

The controller 80 controls an electrical current running to the screw drive 78 and receives electrical power through a conventional electrical lead such as a 110 or 220 volt electrical cord 86. The second force measuring gauge 68 should be able to measure a force in the range of about zero to about 5-10 Newtons to provide the most accurate data. The most important things about the screw drive 76 is that it operate at a reasonably constant speed in any of the speed settings set with the speed knob 82 within its range on the controller 80. The screw drive 76 and controller used in the embodiment shown are a D.C. motor and a voltage rheostat mounted in the controller 80.

The second force measuring gauge 68 most typically can have an output 73 that can be fed to a computer to record the force vs time and to show a curve of the force vs time on a monitor in a well known manner. The time is started by manually by the operator or by the computer program as soon as the computer receives a signal of force greater than zero through the force output 73.

Figure 5:
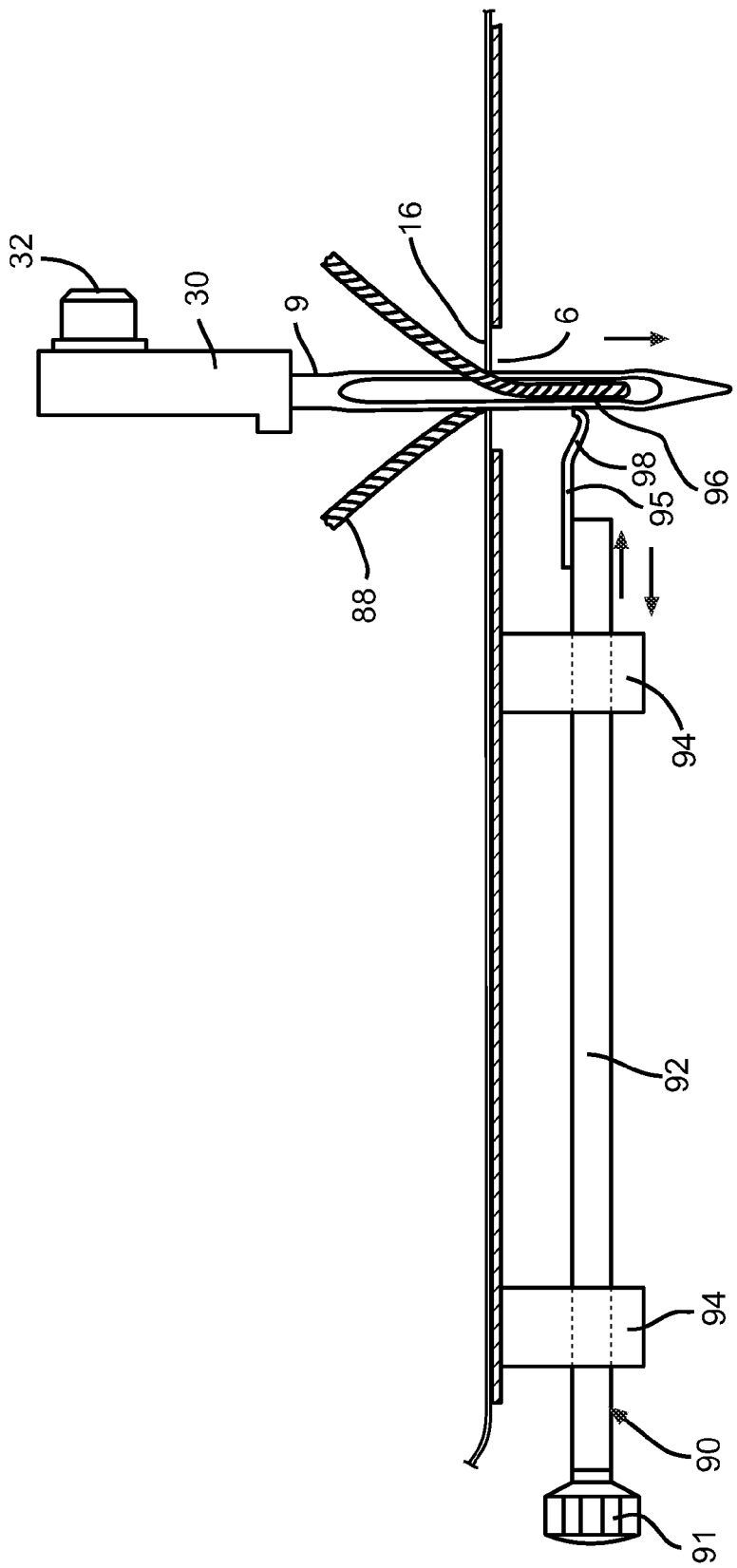
FIG. 5 is an enlarged view of a tufting and tuft holding portion of the apparatus shown in FIGS. 1-4 in a tuft/loop forming position.
Figure 6:
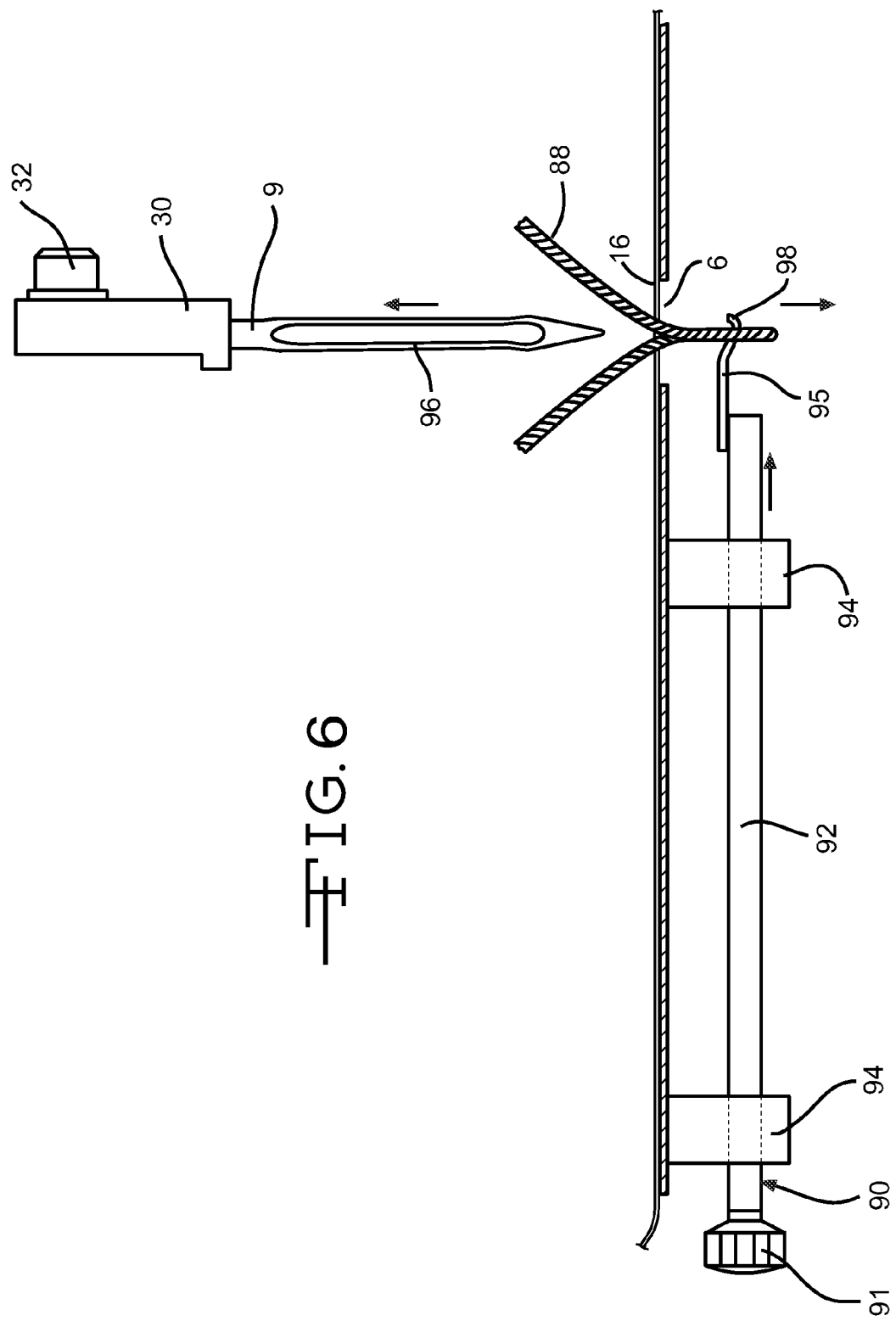
FIG. 6 is an enlarged view of the portion of the apparatus shown in FIG. 5 in a tuft/loop completed position.

Referring now to FIGS. 2, 3, 5 and 6, a manually operated tuft or loop retaining assembly 90 is mounted beneath the top 2 and flat surface 4, see particularly FIGS. 5 and 6. The tuft or loop retaining assembly 90 is comprised of a knob 91 connected to the end of a rod 92 that runs through one or more bushings/guides 94 in such a way that the knob 91 and the rod 92 can move back and forth linearly at least about 1-1.25 inch but this distance is not critical so long as the distance is sufficient that a typical tuft or loop length can be formed. At the end or end portion of the rod 92 is a tuft or loop retainer 95 fixed at a location such that when the knob 91 is moved towards the tufting needle 9 forming the tuft or loop 96 (FIG. 5), the end portion 98 of the tuft or loop retainer moves into a conventional recess (not shown) in the tufting needle 9 and into the tuft or loop 96 so that when the tufting needle 9 is pulled upward and out of the primary backing mat sample 16 by releasing the downward force on the knob 28 allowing the spring 38 to pull the needle holder 30 and tufting needle 9 into its normal position shown in FIGS. 3 and 6, the tuft or loop retainer end portion 98 holds the tuft or loop 96 in the desired location below the bottom surface of the primary backing mat sample 16. A single end of the test yarn is removed from the tufting needle while still holding the loop secure with the loop retainer so as to not disturb the yarn seat in the backing while pulling it from the tufting needle. After removing a single end of the yarn from the tufting needle, the tuft or loop retainer end portion 98 can be withdrawn from the tuft or loop 96 by moving the knob 91 away from the tuft or loop 96 (note that this action is also spring loaded so that the loop retainer withdrawals on its own after releasing pressure on the knob).

The method of using the apparatus of the invention to determine the yarn tuft gripping strength of any candidate for a primary backing mat is described in the following examples.

EXAMPLE 1

A sample strip about 4 inches wide of a primary backing mat product that suffers an undesirably high frequency of tuft pull outs and defects was placed on the apparatus shown in FIGS. 1-6 running through the first sample clamp 8, which was placed in a clamping position by tightening the adjustable bolt 12 appropriately and engaging the DeStaCo clamp 14, across the top 2 lying on the flat surface 4 as the primary backing mat sample 16 and threaded through an open second sample clamp 42. The second sample clamp 42 is raised a half inch or so from its bottom vertical stop and clamped onto the primary backing mat sample 16 by engaging the two DeStaCo clamps 48,50. Next the screw jack 62 is placed into position such that the foot 56 is located just above the horizontal foot 54 of the second sample clamp 42. The rotating wheel 64 of the screw jack 62 is then turned to move the foot 56 down onto the horizontal foot 54 and further until the tension on the primary backing mat sample 16 is 12 lbs. on the sample strip having a width of about 4 inches as indicated by the force measuring gauge 60, in this example a Dillon Model GL 100.

Next a length of yarn, typically 6-8 inches in length and normally the yarn used in making the tufted carpets that the primary backing mat sample is used with, is run through the opening in the tufting needle 9 to about midway of its length. Next, the knob 28 is pushed down to a stop to push the tufting needle 9 and the length of yarn 88 through the primary backing mat sample 16 and through the hole 6 to form a tuft or loop 6 (see FIG. 6). While holding the knob 28 down against a stop, the knob 91 on the tuft or loop retainer assembly 90 is pushed towards the tuft or loop 96 to cause the end portion 98 of the tuft or loop retainer 95 to enter the tuft or loop 96. The downward force on the knob 28 is then removed allowing the tufting needle 9 to return to its starting position above the primary backing mat sample 16 while the end portion of the tuft or loop retainer inside the tuft or loop 96 retains the tuft or loop 96 in a desired position below the bottom surface of the primary backing mat sample 16, in this example the tuft or loop 96 extends about one inch below the bottom surface of the primary backing mat sample 16, but this can vary considerably depending on the specific application the primary backing mat is intended for or used in. A single end of the test yarn is removed from the tufting needle while still holding the loop secure with the loop retainer so as to not disturb the yarn seat in the backing while pulling it from the tufting needle. After removing a single end of the yarn from the tufting needle, the knob 91 can be moved away from the tuft or loop 96 removing the end portion 98 of the tuft or loop retainer 95 out of the tuft or loop 96.

After the desired speed for the screw drive 76 is set by the speed knob 82, in this example one inch per second, the toggle switch knob 84 is pulled cause the screw drive 76 to move the second force measuring gauge 68, the measuring rod 69 and the yarn clamp 71 towards the tufting needle 9 until the yarn clamp 71 is in position to accept an end portion of the yarn 88, and one end portion of the yarn 88 is secured in the yarn clamp 71, the yarn gripping portion of the clamp 71 being positioned above the primary backing mat sample 16 by a distance preferably just high enough that no significant length of the yarn between the yarn clamp and the point where the yarn emerges from the entering surface of the test sample drags on the entering surface of the mat sample during the pulling and also sufficiently high that no part of the yarn clamp 71 or the part of the force gauge holding the yarn clamp 71 contacts the entering surface of the mat test sample, in this example a distance of about 0.12 inch or about 0.125 inch. This distance should be representative of how the yarn is suspended between the top of the tuft or loop 96 and the tufting needle 9 as the primary backing mat is moved with respect to the tufting needles 9 to make the next row of tufts on an industrial tufting production line.

Next, after the second force gauge 68 is set to zero and the computer is readied to receive the force signal, the toggle switch knob 84 is pushed forward to cause the yarn clamp 71 holding the one end portion of the yarn 88 away from the tufting needle until the tuft or loop 96 is pulled totally from the primary backing mat sample 16. During this movement the force on the yarn secured in the yarn clamp 71 will be measured by the second force measuring gauge 68 and fed as a force signal to the computer via the force output 73. A curve showing the force on the yarn 88 between the yarn clamp 71 and the tuft 96 vs time is shown in FIG. 7 and is discussed below.

EXAMPLE 2

Figure 8:
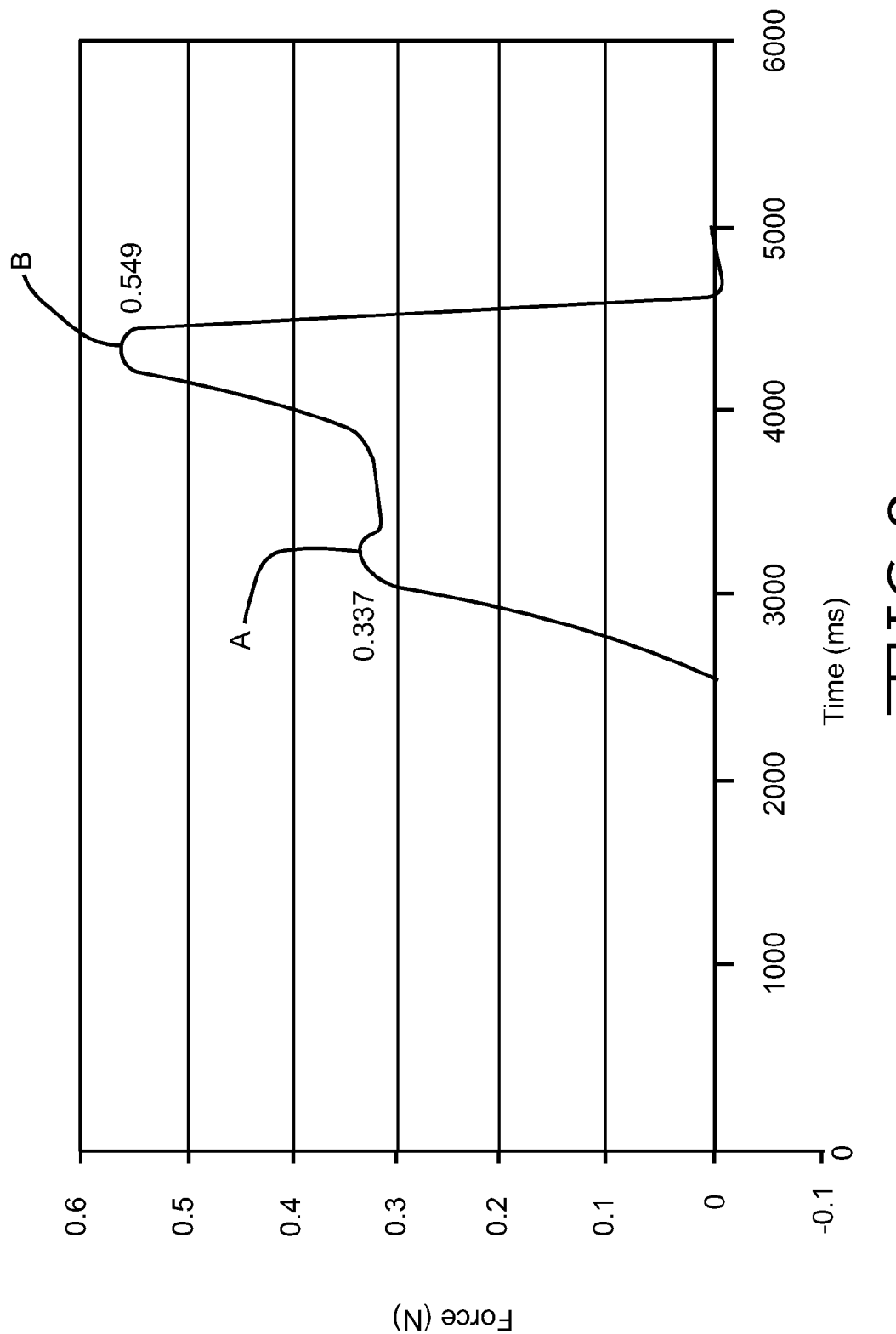
FIG. 8 is a force/time curve for a sample of a different carpet primary backing mat candidate, one having a relative good tuft gripping capability, showing the critical portions of the tuft gripping strength capability of the sample.

A different primary backing mat than the primary backing mat product tested in Example 1 above was tested in the same manner as described in Example 1 and a curve showing the force on the yarn 88 between the yarn clamp 71 and the tuft 96 vs time is shown in FIG. 8 and is discussed below.

Figure 7:
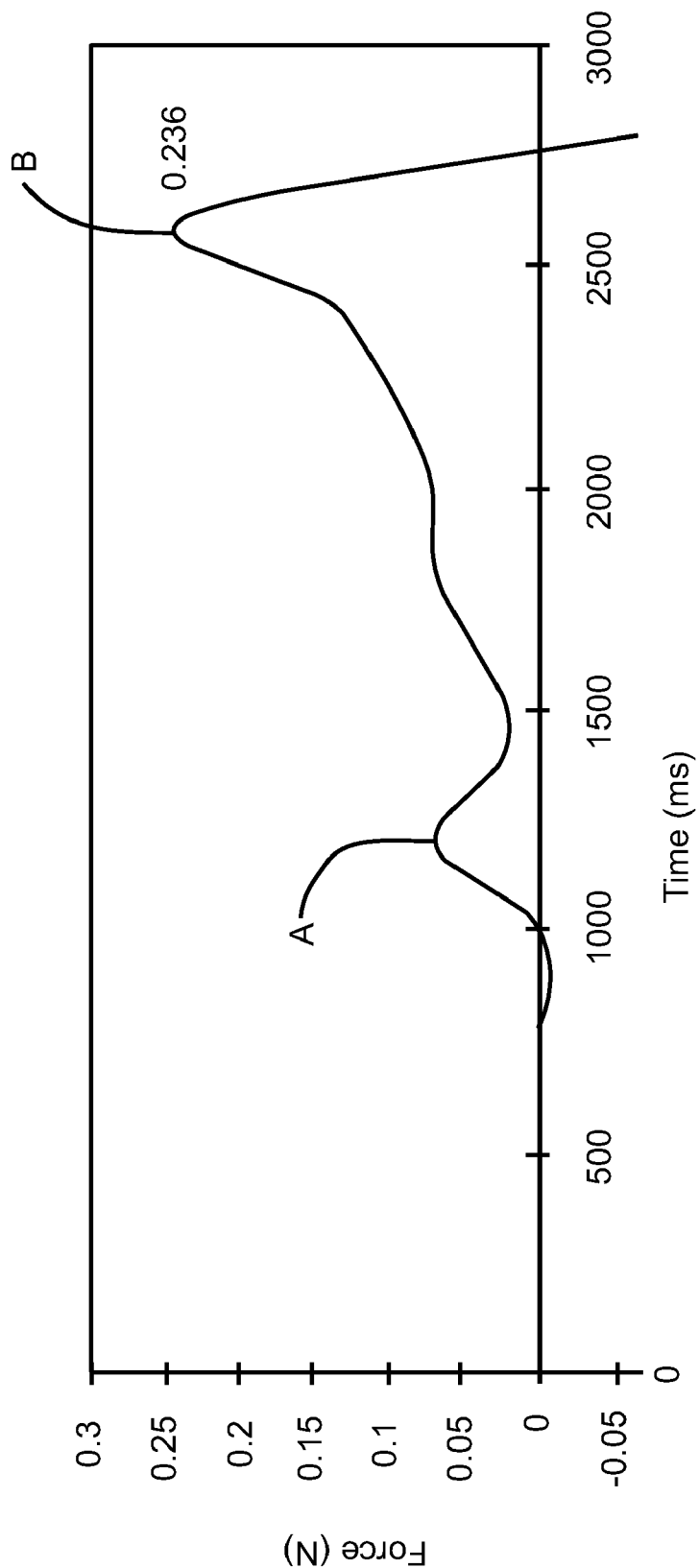
FIG. 7 is a force/time curve for a sample of a carpet primary backing mat candidate showing the critical portions of the tuft gripping strength capability of the sample which is somewhat poor in tuft gripping capability.

Referring to FIG. 7, it is apparent from the results of the test method of this invention why the primary backing mat product tested in Example 1 has an undesirable high frequency of tuft defects and pull-outs. In the curve shown in FIG. 7 there are two force peaks noted by A and B. Force peak A, called a Quality Knee is representative of the force required to start pulling the yarn 88 from the tuft or loop 96, i.e. to shorten the tuft or loop 96. The second force peak B, here called a Defect Peak, is the force required to completely pull the tuft or loop 96 from the primary backing mat sample 16. Prior art test methods of measuring yarn or tuft gripping capability of a primary backing mat only measured the force peak B and didn't indicate the Quality Knee level, the Force Peak A of the current invention. The Quality Knee magnitude is very critical to determining the yarn/tuft gripping capability of a primary backing mat because a shortened tuft or loop is a visual defect that must be corrected with costly labor or a more costly customer complaint will likely occur. Note that following the Quality Knee, Force Peak A, the force in the yarn drops somewhat and levels out for awhile. This is due to the force required to start pulling the one end portion of the yarn 88 out of the primary backing mat is higher than the force required to continue moving the one end portion of the yarn 88 from the primary backing mat, i.e. shortening the tuft or loop 96. Then once the tuft or loop length reaches a certain low height, the force in the yarn again begins to climb due to the resistance of the bottom of the tuft or loop 96 to pull out of the primary backing mat sample.

Using the method and apparatus of the invention to test the primary backing mat used in Example 1 reveals that this primary backing mat product has a very low Quality Knee, Force Peak A, i.e. only about 0.065-0.07 newtons. Thus, this very low Quality Knee of this primary backing mat makes it very vulnerable to overpulling of the yarn strands during the transition from one tuft row to the next tuft and will likely suffer excessive shortening of one or more tufts in the production tufting operation on a loop pile tufting machine. This explains the poorer than desired performance of this primary backing mat product with regard to defective tuft lengths or unintentional rough carpet face, the most frequent type of defect seen on the tufting production line or in the finished carpet. This primary backing mat product also has a much higher Defect Peak, Force Peak B, of about 0.236 newtons, a magnitude that is marginal for tuft or loop pull-out problems. Note that the actual time and force readings will vary with choices of pull speed, needle size, yarn size/type, sample tensions, fabric type, and other variables. Therefore, these actual numbers should only be used as examples under the same or very similar test conditions. The value of the apparatus and test is to compare one fabric to another or to a predetermined benchmark using the same or practically similar conditions.

The primary backing mat tested in Example 2 has a much better record of lower tuft or loop defects and also of fewer tuft or loop pull-outs. The results of the test of the invention on the apparatus of the invention shown in FIG. 8 clearly show the reasons for the better performance of the primary backing mat tested in Example 2. First, the Quality Knee, Force Peak A, occurs at a force of about 0.337 Newtons, about 5 times higher than the Quality Knee of the primary backing mat tested in Example 1. The Defect Peak, Force Peak B, is also more than twice as high at about 0.549 Newtons. However, the latter magnitude is not nearly so important to the performance of the primary backing mat to resist tuft or loop defects as is the magnitude of the Quality Knee, something revealed for the first time in this invention.

The apparatus and method of the invention is particularly as a quality control apparatus and for use in evaluating experimental primary backing mat candidates for maintaining a low tuft or loop defect level and for further reducing or eliminating tuft or loop defects and carpet manufacturing costs.

Note that the actual time and force readings of this test method will vary with choices of pull speed, needle size, yarn size/type, sample tensions, and the particular type of carpet primary backing mat product or candidate and, and as with other comparative tests, when comparing different products or candidates the test variables should be held constant for any series of tests, and should preferably compare favorably, as much as practical, with the variables to be used with the primary backing mat in production.

Different embodiments employing the concept and teachings of the invention will be apparent and obvious to those of ordinary skill in this art and these embodiments are likewise intended to be within the scope of the claims. For example, manual steps and features in the method and apparatus could be mechanized or automated using known elements and techniques. The inventor does not intend to abandon any disclosed inventions that are reasonably disclosed but do not appear to be literally claimed below, but rather intends those embodiments to be included in the broad claims either literally or as equivalents to the embodiments that are literally included.

The invention claimed is:

1. An apparatus for quickly and accurately measuring the capability of a primary backing mat to grip yarn forming tufts or loops of yarn in a manner that resists overshortening of tufts and snags that pull yarn in a direction that would reduce the height of one or more of the tufts or loops or that would pull one or more loops completely from the primary backing mat, any of which cause defects in the tufted interim product that if not repaired cause defects in finished tufted carpet or carpet tiles, the apparatus comprising;
   a) a top or generally flat surface having an opening therein to support a primary backing mat test sample and that allows a tufting needle to pass through a test sample of primary backing mat and the opening in the table top or flat surface,
   b) a first clamp on a first side portion of the table or flat surface to secure a test sample of primary backing mat,
   c) a second clamp that is movable on an opposite side of the table or flat surface for securing the test sample spaced from the first clamp, the second clamp being movable to apply a desired tension on the test sample,
   d) a mechanism for moving the second clamp to apply a desired tension force on the test sample,
   e) a movable tufting needle holder, holding a tufting needle, for moving the tufting needle in a generally perpendicular direction with respect to the first surface of the test sample to cause the tufting needle and a length of yarn to pass therethrough penetrating the first surface of the test sample, the test sample and the second surface of the test sample and to form a tuft or loop of yarn extending from the second surface of the test sample,
   f) a movable tuft or loop keeper for holding and moving a tuft or loop keeper into and out of a tuft or loop keeping position,
   g) a yarn clamp located adjacent and above the first surface of the test sample for securing an end part of the length of yarn and located sufficiently above the first surface that the yarn portion between the yarn clamp and the location where the yarn emerges through the first surface of the test sample does not contact the first surface of the test sample over a significant portion of the yarn portion,
   h) a force measuring device for holding the yarn clamp and for measuring continuously the force required to pull the end portion of yarn, including the tuft or loop, out of the test sample,
   i) a mechanism for moving the force measuring device holding the yarn clamp in a direction and manner such that the yarn clamp moves generally parallel to the first surface of the test sample and away from the tuft or loop until the loop is pulled completely out of the test sample and
   j) a device for recording the continuous force on the end portion of the yarn, measured by the force measuring device versus time, at least until the tuft or loop has been pulled completely out of the test sample.

2. The apparatus of claim 1 wherein the device in j for recording is a computer.

3. The apparatus of claim 1 wherein the tufting needle holder is biased to return the tufting needle to a starting position after a force applied to push the tufting needle through the sample has been removed.

4. The apparatus of claim 2 wherein the tufting needle holder is biased to return the tufting needle to a starting position after a force applied to push the tufting needle through the sample has been removed.

5. The apparatus of claim 1 wherein the yarn clamp is located such that it grips the end portion of the yarn a distance about 0.125 inch above the top surface of the sample.

6. The apparatus of claim 2 wherein the yarn clamp is located such that it grips the end portion of the yarn a distance about 0.125 inch above the top surface of the sample.

7. The apparatus of claim 3 wherein the yarn clamp is located such that it grips the end portion of the yarn a distance about 0.125 inch above the top surface of the sample.

8. A method for quickly and accurately measuring the capability of a primary backing mat to grip a tuft or loop of yarn in a manner that resists yarn pulling momentum and snags that pull yarn in a direction that would reduce the height of one or more of the loops or remove one or more loops completely from the primary backing mat causing defects in the tufted interim product, and if not repaired, defects in the finished tufted carpet or carpet tiles, the method comprising;
   a) applying a desired tension onto a strip of primary backing mat, a test sample,
   b) forcing a tufting needle holding a length of yarn through a first surface, thickness and a second surface of the test sample in a generally perpendicular direction to the first and second surfaces of the test sample to form a loop of yarn extending from the second surface of the test sample,
   c) holding the loop of yarn in place while the tufting needle holding the length of yarn is withdrawn, in a generally perpendicular direction to the second and first surfaces of the test sample, from the test sample,
   d) placing one end portion of the length of yarn extending from the first surface of the test sample into a yarn clamp mounted on a force measuring device,
   e) moving the yarn clamp in a direction generally parallel to the first surface and away from the tuft in the test sample at a generally consistent speed while continuously measuring and recording the force necessary to pull the length of yarn from the test sample and to completely remove the loop from the second surface and the first surface of the test sample.

9. The method of claim 8 wherein the tension applied to the test sample is the same or very similar to the tension that will be applied to the primary backing mat on commercial tufting lines.

10. The method of claim 8 wherein the yarn clamp is positioned to grip the one end portion of the length of yarn such that it is about 0.12 inch above the top surface of the yarn sample.

11. The method of claim 9 wherein the yarn clamp is positioned to grip the one end portion of the length of yarn such that it is about 0.12 inch above the top surface of the yarn sample.

12. The method of claim 8 wherein the recording of the force versus time is done with a computer.

13. The method of claim 9 wherein the recording of the force versus time is done with a computer.

14. The method of claim 10 wherein the recording of the force versus time is done with a computer.

15. The method of claim 11 wherein the recording of the force versus time is done with a computer.

* * * * *